US006743269B2

(12) United States Patent
Meyer et al.

(10) Patent No.: US 6,743,269 B2
(45) Date of Patent: Jun. 1, 2004

(54) GRANULES BASED ON PYROGENICALLY PRODUCED ALUMINIUM OXIDE, PROCESS FOR THE PRODUCTION THEREOF AND USE THEREOF

(75) Inventors: Juergen Meyer, Stockstadt (DE); Peter Neugebauer, Offenbach (DE); Martin Steigerwald, Wiesen (DE)

(73) Assignee: Degussa AG, Duesseldorf (DE)

( * ) Notice: Subject to any disclaimer, the term of this patent is extended or adjusted under 35 U.S.C. 154(b) by 109 days.

(21) Appl. No.: 10/212,221

(22) Filed: Aug. 6, 2002

(65) Prior Publication Data

US 2003/0119655 A1 Jun. 26, 2003

(30) Foreign Application Priority Data

Aug. 6, 2001 (DE) .......................... 101 38 574

(51) Int. Cl.[7] .............. C09K 3/14; C01F 7/30; C09C 1/40; B01J 21/04; B01J 2/00
(52) U.S. Cl. .................. 51/309; 501/127; 502/355; 502/414; 424/691; 106/3; 106/401; 423/625
(58) Field of Search .................. 501/127, 48, 59, 501/62, 66, 68; 502/355, 414; 424/691; 51/309; 106/3, 401; 423/625

(56) References Cited

U.S. PATENT DOCUMENTS

| 4,902,570 A | 2/1990 | Heinemann et al. |
| 5,024,685 A | 6/1991 | Torok et al. |
| 5,384,194 A | 1/1995 | Deusser et al. |
| 5,424,258 A | 6/1995 | Mangold et al. |
| 5,501,933 A | 3/1996 | Deusser et al. |
| 6,197,073 B1 | 3/2001 | Kadner et al. |
| 6,197,469 B1 | 3/2001 | Kerner et al. |
| 6,303,256 B1 | 10/2001 | Kerner et al. |

FOREIGN PATENT DOCUMENTS

| DE | 39 02 913 | 8/1990 |
| DE | 40 35 089 | 4/1992 |
| DE | 42 02 694 | 7/1993 |
| DE | 199 43 291 | 3/2001 |
| EP | 1 083 151 | 3/2001 |

*Primary Examiner*—Michael Marcheschi
(74) *Attorney, Agent, or Firm*—Oblon, Spivak, McClelland, Maier & Neustadt, P.C.

(57) ABSTRACT

Granules based on aluminium oxide having the characteristics:

| Average grain diameter: | 5.0 to 150 μm |
| Tamped density: | 300 to 1200 g/l |

The granules are produced by dispersing aluminium oxide in water, performing spray drying, optionally heat treatment and/or silanization. In silanized form, the granules have the following characteristics:

| Average grain diameter: | 5 to 160 μm |
| Tamped density: | 300 to 1200 g/l |
| Carbon content: | 0.3 to 12.0 wt. % |

The granules are used inter alia as catalyst supports, in cosmetics, in toner powders, in paints and lacquers, as abrasives and polishing agents and as a raw material in the production of glass and ceramics.

19 Claims, No Drawings

GRANULES BASED ON PYROGENICALLY PRODUCED ALUMINIUM OXIDE, PROCESS FOR THE PRODUCTION THEREOF AND USE THEREOF

BACKGROUND OF THE INVENTION

1. Field of the Invention

The present invention relates to granules based on pyrogenically produced aluminium oxide, to the process for the production thereof, and to the use thereof.

2. Description of the Background

It is known to produce pyrogenic aluminium oxide by means of elevated temperature or flame hydrolysis from $AlCl_3$ (Ullmanns Enzyklopädie der technischen Chemie, 4th edition, volume 21, page 464 (1982)).

Pyrogenic aluminium oxides are distinguished by extreme fineness, correspondingly elevated specific surface area (BET), very high purity, spherical particle shape and the absence of pores. Due to these properties, there is increasing interest in pyrogenically produced aluminium oxides as supports for catalysts (D. Koth et al, Chem. Ing. Techn. 52, 628 (1980)). For this application, the pyrogenically produced aluminium oxide is mechanically formed, for example by means of tabletting machines.

SUMMARY OF THE INVENTION

The object accordingly arose of providing sprayed granules of pyrogenically produced aluminium oxide which may be used for a variety of purposes, such as, for example, catalyst supports.

It is another object of the invention to provide methods of making and using such granules, as well as to provide compositions containing the same.

The objects of the present invention, and others, may be accomplished with granules comprising, i.e., based on, pyrogenically produced aluminium oxide having the following physicochemical characteristics:

| | |
|---|---|
| Average grain diameter: | 5.0 to 150 $\mu$m |
| Tamped density: | 300 to 1200 g/l. |

The objects of the invention may also be accomplished with granules comprising pyrogenicaly produced aluminium oxide having the following physicochemical characteristics:

| | |
|---|---|
| Average grain diameter: | 5 to 160 $\mu$m |
| Tamped density: | 300 to 1200 g/l |
| Carbon content: | 0.3 to 12.0 wt. %. |

The objects of the invention may also be accomplished with a process for the production of the granules described above, comprising dispersing pyrogenically produced aluminium oxide is dispersed in water and then spray drying.

The objects of the invention may also be accomplished with a composition selected from the group consisting of a catalyst support, glass, ceramic, abrasive agent, polishing agent, cosmetic, toner powder, paint and lacquer, which comprises the granules described above, and with methods of making the composition.

A more complete appreciation of the invention and many of the attendant advantages thereof will be readily obtained as the same becomes better understood by reference to the detailed description below.

DETAILED DESCRIPTION OF THE INVENTION

As described above, the average grain diameter of the inventive granules may be 5.0 to 150 $\mu$m and the tamped density may be 300 to 1200 g/l. In a preferred embodiment of the invention, the granules may exhibit an average grain diameter of 5.0 to 45 $\mu$m and a tamped density of 300 to 550 g/l. These ranges for the average grain diameter include all specific values and subranges therebetween, such as 10, 15, 20, 25, 50, 75, 100 and 125 $\mu$m. These ranges for the tamped density include all specific values and subranges therebetween, such as 350, 400, 500, 600, 700, 800, 900, 1000 and 1100 g/l.

The granules according to the invention may be produced by dispersing pyrogenically produced aluminium oxide in water, spray drying it and optionally heat treating the granules obtained at a temperature of 150 to 1100° C. for a period of 1 to 8 hours. This temperature range includes all specific values and subranges therebetween, such as 200, 250, 300, 400, 500, 600, 700, 800, 900, and 1000° C. This range for the time period includes all specific values and subranges therebetween, such as 2, 3, 4, 5, 6, and 7 hours.

The educt used may comprise an aluminium oxide as described in Ullmanns Enzyklopädie der technischen Chemie, 4th edition, volume 21, page 464(1982), incorporated herein by reference. Another educt which may be used is a pyrogenically produced aluminium oxide with an elevated surface area, which exhibits a BET specific surface area of greater than 115 $m^2/g$, and the Sears value is greater than 8 ml/2 g.

Measured on a sample weight of 16 g, the dibutyl phthalate absorption of this aluminium oxide powder is not measurable (no detectable end point).

This pyrogenically produced aluminium oxide may be produced using the flame oxidation or preferably the flame hydrolysis method, wherein the starting material used is a vaporisable aluminium compound, preferably the chloride. This aluminium oxide is described in DE 199 42 291.0-41, incorporated herein by reference.

The present invention also provides granules based on pyrogenically produced aluminium oxide having the following physicochemical characteristics:

| | |
|---|---|
| Average grain diameter: | 5 to 160 $\mu$m |
| Tamped density: | 300 to 1200 g/l, preferably 300–600 g/l |
| Carbon content: | 0.3 to 12.0 wt. %, preferably 1.0 to 6.0 wt. % |

The granules according to the invention may be produced by dispersing pyrogenically produced aluminium oxide in water, spray drying it, optionally heat treating the granules obtained at a temperature of 150 to 1000° C. for a period of 1 to 8 hours and then silanizing them.

Silanization may be performed using halosilanes, alkoxysilanes, silazanes and/or siloxanes.

The following substances may in particular be used as organosilanes:

| | |
|---|---|
| (a) | Organosilanes of the type $(RO)_3Si(C_nH_{2n+1})$ and $(RO)_3Si(C_nH_{2n-1})$ <br> R = alkyl, such as for example methyl, ethyl, n-propyl, i-propyl, butyl <br> n = 1–20 |
| (b) | Organosilanes of the type $R'_x(RO)_ySi(C_nH_{2n+1})$ and $R'_x(RO)_ySi(C_nH_{2n-1})$ <br> R = alkyl, such as for example methyl, ethyl, n-propyl, i-propyl, butyl <br> R' = alkyl, such as for example methyl, ethyl, n-propyl, i-propyl, butyl <br> R' = cycloalkyl <br> n = 1–20 <br> x+y = 3 <br> x = 1.2 <br> y = 1.2 |
| (c) | Haloorganosilanes of the type $X_3Si(C_nH_{2n+1})$ and $X_3Si(C_nH_{2n-1})$ <br> X = Cl, Br <br> n = 1–20 |
| (d) | Haloorganosilanes of the type $X_2(R')Si(C_nH_{2n+1})$ and $X_2(R')Si(C_nH_{2n-1})$ <br> X = Cl, Br <br> R' = alkyl, such as for example methyl, ethyl, n-propyl, i-propyl, butyl <br> R' = cycloalkyl <br> n = 1–20 |
| (e) | Haloorganosilanes of the type $X(R')_2Si(C_nH_{2n+1})$ and $X(R')_2Si(C_nH_{2n-1})$ <br> X = Cl, Br <br> R' = alkyl, such as for example methyl, ethyl, <br> R' = cycloalkyl, n-propyl, i-propyl, butyl <br> n = 1–20 |
| (f) | Organosilanes of the type $(RO)_3Si(CH_2)_m$-R' <br> R = alkyl, such as methyl, ethyl, propyl <br> m = 0.1–20 <br> R' = methyl, aryl (for example $C_6H_5$, substituted phenyl residues) <br> —$C_4F_9$, $OCF_2$—CHF—$CF_3$, —$C_6F_{13}$, —O—$CF_2$—$CHF_2$ <br> —$NH_2$, —$N_3$, —SCN, —CH=$CH_2$, —NH—$CH_2$—$CH_2$—$NH_2$, <br> —N—($CH_2$—$CH_2$—$NH_2)_2$ <br> —OOC($CH_3$)C=$CH_2$ <br> —$OCH_2$—CH(O)$CH_2$ <br> —NH—CO—N—CO—$(CH_2)_5$ <br> —NH—COO—$CH_3$, —NH—COO—$CH_2$—$CH_3$, —NH—$(CH_2)_3Si(OR)_3$ <br> —$S_x$—$(CH_2)_3Si(OR)_3$ <br> —SH <br> - NR'R"R'" (R' = alkyl, aryl; R" = H, alkyl, aryl; R'" = H, alkyl, aryl, benzyl, $C_2H_4$NR"" R'"" where R"" = H, alkyl and R'"" = H, alkyl) |
| (g) | Organosilanes of the type $(R")_x(RO)_ySi(CH_2)_m$-R' <br> R" = alkyl    x+y = 2 <br> = cycloalkyl    x = 1.2 <br>                y = 1.2 <br>                m = 0.1 to 20 <br> R' = methyl, aryl (for example $C_6H_5$, substituted phenyl residues) <br> —$C_4F_9$, $OCF_2$—CHF—$CF_3$, —$C_6F_{13}$, —O—$CF_2$—$CHF_2$ <br> —$NH_2$, —$N_3$, —SCN, —CH=$CH_2$, —NH—$CH_2$—$CH_2$—$NH_2$, <br> —N—($CH_2$—$CH_2$—$NH_2)_2$ <br> —OOC($CH_3$)C=$CH_2$ <br> —$OCH_2$—CH(O)$CH_2$ <br> —NH—CO—N—CO—$(CH_2)_5$ <br> —NH—COO—$CH_3$, —NH—COO—$CH_2$—$CH_3$, —NH—$(CH_2)_3Si(OR)_3$ <br> —$S_x$—$(CH_2)_3Si(OR)_3$ <br> —SH - NR'R"R'" (R' = alkyl, aryl; R" = H, alkyl, aryl; R'" = H, alkyl, aryl, benzyl, $C_2H_4$NR"" R'"" where R"" = H, alkyl and R'"" = H, alkyl) |
| (h) | Haloorganosilanes of the type $X_3Si(CH_2)_m$-R' <br> X = Cl, Br <br> m = 0.1–20 <br> R' = methyl, aryl (for example —$C_6H_5$, substituted phenyl residues) <br> —$C_4F_9$, $OCF_2$—CHF—$CF_3$, —$C_6F_{13}$, —O—$CF_2$—$CHF_2$ <br> —$NH_2$, —$N_3$, —SCN, —CH=$CH_2$, <br> —NH—$CH_2$—$CH_2$—$NH_2$, <br> —N—($CH_2$—$CH_2$—$NH_2)_2$ <br> —OOC($CH_3$)C=$CH_2$ <br> —$OCH_2$—CH(O)$CH_2$ <br> —NH—CO—N—CO—$(CH_2)_5$ <br> —NH—COO—$CH_3$, —NH—COO—$CH_2$—$CH_3$, —NH—$(CH_2)_3Si(OR)_3$ <br> —$S_x$—$(CH_2)_3Si(OR)_3$ <br> —SH |

-continued

| | |
|---|---|
| (i) | Haloorganosilanes of the type $(R)X_2Si(CH_2)_m\text{-}R'$ |
| | X = Cl, Br |
| | R = alkyl, such as methyl, ethyl propyl |
| | m = 0.1–20 |
| | R' = methyl, aryl (for example $-C_6H_5$, substituted phenyl residues) |
| | $-C_4F_9$, $OCF_2-CHF-CF_3$, $-C_6F_{13}$, $-O-CF_2-CHF_2$ |
| | $-NH_2$, $-N_3$, $-SCN$, $-CH=CH_2$, $-NH-CH_2-CH_2-NH_2$, |
| | $-N-(CH_2-CH_2-NH_2)_2$ |
| | $-OOC(CH_3)C=CH_2$ |
| | $-OCH_2-CH(O)CH_2$ |
| | $-NH-CO-N-CO-(CH_2)_5$ |
| | $-NH-COO-CH_3$, $-NH-COO-CH_2-CH_3$, $-NH-(CH_2)_3Si(OR)_3$, wherein R may be methyl, ethyl, propyl, butyl |
| | $-S_x-(CH_2)_3Si(OR)_3$, wherein R may be methyl, ethyl, propyl, butyl |
| | $-SH$ |
| (j) | Haloorganosilanes of the type $(R)_2X\,Si(CH_2)_m\text{-}R'$ |
| | X = Cl, Br |
| | R = alkyl |
| | m = 0.1–20 |
| | R' = methyl, aryl (for example $-C_6H_5$, substituted phenyl residues) |
| | $-C_4F_9$, $OCF_2-CHF-CF_3$, $-C_6F_{13}$, $-O-CF_2-CHF_2$ |
| | $-NH_2$, $-N_3$, $-SCN$, $-CH=CH_2$, $-NH-CH_2-CH_2-NH_2$, |
| | $-N-(CH_2-CH_2-NH_2)_2$ |
| | $-OOC(CH_3)C=CH_2$ |
| | $-OCH_2-CH(O)CH_2$ |
| | $-NH-CO-N-CO-(CH_2)_5$ |
| | $-NH-COO-CH_3$, $-NH-COO-CH_2-CH_3$, $-NH-(CH_2)_3Si(OR)_3$ |
| | $-S_x-(CH_2)_3Si(OR)_3$ |
| | $-SH$ |
| (k) | Silazanes of the type $R'R_2Si-N(H)-SiR_2R'$ |
| | R = alkyl |
| | R' = alkyl, vinyl |
| (l) | Cyclic polysiloxanes of the type D 3, D 4, D 5, wherein D 3, D 4 and D 5 are taken to mean cyclic polysiloxanes having 3, 4 or 5 units of the type $-O-Si(CH_3)_2-$. For example, octamethylcyclotetrasiloxane = D 4 |

$$\begin{array}{c} H_3C \\ H_3C \end{array} Si \begin{array}{c} O \\ O \end{array} Si \begin{array}{c} CH_3 \\ CH_3 \end{array}$$

(structure: octamethylcyclotetrasiloxane)

| | |
|---|---|
| (m) | Polysiloxanes or silicone oils of the type |

$$Y-O-\left(\left(\begin{array}{c}R\\|\\Si-O\\|\\R'\end{array}\right)_m\left(\begin{array}{c}R''\\|\\Si-O\\|\\R'''\end{array}\right)_n\right)_u-Y$$

| | |
|---|---|
| m = | 0, 1, 2, 3, ... ∞ |
| n = | 0, 1, 2, 3, ... ∞ |
| u = | 0, 1, 2, 3, ... ∞ |
| Y = | $CH_3$, H, $C_nH_{2n+1}$ n = 1–20 |
| Y = | $Si(CH_3)_3Si(CH_3)_2H$ |
| | $Si(CH_3)_2OH$, $Si(CH_3)_2(OCH_3)$ |
| | $Si(CH_3)_2(C_nH_{2n+1})$ n = 1–20 |
| R = | alkyl, such as $C_nH_{2n+1}$, wherein n is 1 to 20, aryl, such as phenyl and substituted phenyl residues, $(CH_2)_n-NH_2$ (n = 0, 1, 2, ... 20), H |
| R' = | alkyl, such as $C_nH_{2n+1}$, wherein n is 1 to 20, aryl, such as phenyl and substituted phenyl residues, $(CH_2)_n-NH_2$ (n = 0, 1, 2, ... 20), H |
| R'' = | alkyl, such as $C_nH_{2n+1}$, wherein n is 1 to 20, aryl, such as phenyl and substituted phenyl residues, $(CH_2)_n-NH_2$ (n = 0, 1, 2, ... 20), H |
| R''' = | alkyl, such as $C_nH_{2n+1}$, wherein n is 1 to 20, aryl, such as phenyl and substituted phenyl residues, $(CH_2)_n-NH_2$ (n = 0, 1, 2, ... 20), H |

The dispersion in water may exhibit an aluminium oxide concentration of 3 to 25 wt. %.

Organic auxiliary substances may be added to the dispersion in order to increase the stability of the dispersion and to improve particle morphology after spray drying.

The following auxiliary substances may, for example, be used: polyalcohols, polyethers, fluorocarbon-based surfactants, alcohols.

Spray drying may be performed at a temperature of 200 to 600° C., using disk atomisers or nozzle atomisers, such as for example a single-fluid or two-fluid nozzle.

Heat treatment of the granules may be performed both in a stationary bed, such as for example in chamber kilns, and in a moving bed, such as for example rotary tube dryers.

Silanization may be performed with the same halosilanes, alkoxysilanes, silazanes and/or siloxanes as described above, wherein the silanising agent may optionally be dissolved in an organic solvent, such as for example ethanol.

The silanes trimethoxyoctylsilane, hexamethyldisilazane, aminopropyltriethoxysilane, dimethylpolysiloxane, hexadecyltrimethoxysilane and 3-methacryloxypropyltrimethoxysilane may preferably be used as the silanising agent.

Silanization may be performed by spraying the granules with the silanising agent at room temperature and then heat treating the mixture at a temperature of 105 to 400° C. for a period of 1 to 6 hours.

Silanization of the granules may alternatively be performed by treating the granules with the silanizing agent in vapour form and then heat treating the mixture at a temperature of 200 to 800° C. for a period of 0.5 to 6 h.

Heat treatment may be performed under protective gas, such as for example nitrogen.

Silanization may be performed continuously or batchwise in heatable mixers and dryers with sprayers. Suitable apparatuses may be, for example: plough bar mixers, disk dryers, fluidized or turbulent bed dryers.

By varying the feedstock, the conditions during spraying, heat treatment and silanization, it is possible to modify the physicochemical characteristics of the granules, such as specific surface area, grain size distribution, tamped density and pH value, within the stated ranges.

The aluminium oxide granules according to the invention exhibit the following advantages:
Flow behaviour is better than for aluminium oxide which has not been spray dried.
Incorporation into organic systems is easier.
Dispersion is simpler.
No additional auxiliary substances are required for granulation.
In comparison with aluminium oxide which has not been spray dried and does not exhibit a defined agglomerate size, the aluminium oxide granules according to the invention have a defined particle size.
The aluminium oxide granules according to the invention make dust-free handling possible.
Due to the elevated tamped density, transport packaging costs are reduced.
The aluminium oxide granules according to the invention may be used as a catalyst support.
Aluminium oxide which has not been spray dried is not suitable for this purpose because it is, for example, entrained from the fluidized bed.

The granules according to the invention may be used as supports for catalysts, and in cosmetics, in toner powders, in paints and lacquers, as abrasives and polishing agents and as a raw material in the production of glass and ceramics.

The granules may be modified in various ways.

Examples of Modification are:
Incorporation of cations, such as for example $H^+$, $Cs^+$, rare earth metal or noble metal cations.
Incorporation of materials or metal oxides by reaction with suitable precursor molecules, such as for example $TiCl_4$, $TiBr_4$, $Ti(OEt)_4$, $TiCp_2Cl_2$ (Cp=cyclopentadienyl), $Mn_2(CO)_{10}$, $Fe(CO)_5$.
Incorporation of noble metals or metal oxides by impregnation with solutions of the metal or noble metal salts.

The granules according to the invention may be used as catalysts and catalyst supports, for example for the following catalytic reactions:

Oxy-functionalization of hydrocarbons, oxidation of olefins to yield epoxides with hydrogen peroxide, alkyl or aryl hydroperoxides, such as for example tert.-butyl hydroperoxide or phenylethyl hydroperoxide ($C_6H_5CH_2CH_2OOH$) and/or oxygen, alkylation of aromatics, hydrogenations, dehydrogenation, hydration, dehydrations, isomerizations, addition and elimination reactions, nucleophilic and electrophilic substitution reactions, hydroxylations of aromatics and heteroaromatics, epoxy/aldehyde rearrangements, amminations, ammoximations, polymerization reactions, esterification and etherification reactions, as well as catalytic nitrogen oxide removal.

The granules according to the invention are moreover suitable as supports for dyes, perfumes and active substances.

EXAMPLES

Having generally described this invention, a further understanding can be obtained by reference to certain specific examples which are provided herein for purposes of illustration only and are not intended to be limiting unless otherwise specified.

Example 1

In a burner of known design, 320 kg/h of previously vaporized aluminium trichloride ($AlCl_3$) are combusted together with 100 $Nm^3/h$ of hydrogen and 450 $Nm^3/h$ of air.

After the flame reaction, the finely divided aluminium oxide with an elevated surface area is separated from the simultaneously produced hydrochloric-acid gases in a filter or cyclone, wherein any remaining traces of HCl are removed by treatment with humidified air at elevated temperature.

The resultant pyrogenic aluminium oxide with an elevated surface area here exhibits the physicochemical characteristics shown in Table 1. Table 1 also shows, by way of comparison, data for the commercially available pyrogenic aluminium oxide from Degussa-Hüls AG, Frankfurt. (Commercial name Aluminium oxide C)

TABLE 1

| | Unit | Aluminium oxide with an elevated surface area according to the invention Alu 130 | Aluminium oxide C |
|---|---|---|---|
| BET specific surface area | $m^2/g$ | 121 | 100 |
| Sears value (pH 4 to 9) | ml/2 g | 9.38 | 7.05 |
| Ph | 4% aqueous dispersion | 4.93 | 4.5 |

TABLE 1-continued

|  | Unit | Aluminium oxide with an elevated surface area according to the invention Alu 130 | Aluminium oxide C |
|---|---|---|---|
| Drying loss | wt. % | 3.3 | 3.0 |
| Bulk density | g/l | 55 | 48 |
| Tamped density | g/l | 63 | 57 |
| DBP absorption | wt. % | not measurable, no end point detectable. | 231 |

DBP: dibutyl phthalate
Measurement of the Sears value is described in EP 0 717 088.

Example 2

An aluminium oxide with the following physicochemical characteristics is used as the progenically produced aluminium oxide. It is known from the pigments publication series no. 56 "Highly disperse metal oxides from the Aerosil process", 4th edition, February 1989, Degussa AG.

|  |  | Aluminium oxide C |
|---|---|---|
| CAS reg. no. |  | 1344-28-1 |
| BET surface area[1] | $m^2/g$ | 100 ± 15 |
| Average primary particle size | nm | 13 |
| Tamped density[2] | g/l | approx. 80 |
| Weight per unit volume[10] | g/ml | approx. 3.2 |
| Drying loss[3] on leaving the supplier's works (2 hours at 105° C.) | % | <5 |
| Ignition loss[4][7] (2 hours at 1000° C.) | % | <3 |
| pH value[5] (in 4% aqueous dispersion) |  | 4.5–5.5 |
| $SiO_2$[8] |  | <0.1 |
| $Al_2O_3$[8] |  | <99.6 |
| $Fe_2O_3$[8] |  | <0.2 |
| $TiO_2$[8] |  | >0.1 |
| $ZrO_2$[8] |  | — |
| $HfO_2$[8] |  | — |
| $HCl$[8][9] |  | <0.5 |
| Screen oversize[6] (Mocker method, 45 μm) | % | <0.05 |

[1]to DIN 66131
[2]to DIN ISO 787/XI, JIS K 5101/18 (unscreened)
[3]to DIN ISO 787/II, ASTM D 280, JIS K 5101/21
[4]to DIN 55921, ASTM D 1208, JIS K 5101/23
[5]to DIN ISO 787/IX; ASTM D 1208, JIS K 5101/24
[6]to DIN ISO 787/XVIII; JIS K 5101/20
[7]relative to material dried for 2 hours at 105° C.
[8]relative to material calcined for 2 hours at 1000° C.
[9]HCl content is part of ignition loss
[10]determined using air comparison pycnometer The aluminium oxides are produced by spraying a volatile aluminium compound into a detonating gas flame of hydrogen and air. In most cases, aluminium trichloride is used. This substance hydrolyses under the action of the water generated in the detonating gas reaction to yield aluminium oxide and hydrochloric acid. After leaving the flame, the aluminium oxide enters a so-called coagulation zone, in which the aluminium oxide primary particles and primary aggregates agglomerate. The product, which at this stage is in the form of a kind of aerosol, is separated from the gaseous accompanying substances in cyclones and is then post-treated with moist hot air.

The particle sizes of the aluminium oxides obtained in this manner may be varied by means of the reaction conditions, such as for example flame temperature, hydrogen or oxygen content, quantity of aluminium trichloride, the residence time in the flame or the length of the coagulation section.

The physico-chemical characteristics are determined using the following measurement methods:

The BET surface area is determined with nitrogen to DIN 66 131.

Determination of tamped density in accordance with DIN ISO 787/XI.

Basis of Tamped Density Determination

Tamped density (formerly tamped volume) is equal to the quotient of mass and volume of a powder after tamping in a jolting volumeter under defined conditions. According to DIN ISO 787/XI, tamped density is stated in $g/cm^3$. However, due to the very low tamped density of pyrogenic oxides, we have stated the value in g/l. The drying and screening and the repetition of the tamping operation are also omitted.

Equipment for Determining Tamped Density

Jolting volumeter

Measuring cylinder

Laboratory balance (readability 0.01 g)

Performance of Tamped Density Determination

200±10 ml of granules are poured into the measuring cylinder of the jolting volumeter in such a manner that no cavities remain and the surface is horizontal.

The mass of the introduced sample is weighed to an accuracy of 0.01 g. The measuring cylinder containing the sample is placed in the holder on the jolting volumeter and tamped 1250 times.

Evaluation of Tamped Density Determination $$\text{Tamped density}(g/l) \frac{G \text{ sample weight} \times 1000}{\text{ml volume reading}}$$

The pH value is determined in a 4% aqueous dispersion, in the case of hydrophobic catalyst supports in 1:1 water-:methanol.

Reagents for pH Value Determination

Distilled or deionized water, pH>5.5

Methanol, analytical grade

Buffer solution, pH 7.00 pH 4.66

Equipment for RH Value Determination

Laboratory balance (readability 0.1 g)

Glass beaker, 250 ml

Magnetic stirrer

Magnetic stirrer bar, length 4 cm

Combined pH electrode pH meter

Dispensing bottle, 100 ml

Operating Procedure for Determining pH Value

Determination is performed in accordance with DIN/ISO 787/IX:

Calibration: Before the pH value is measured, the meter is calibrated with the buffer solutions. If several measurements are performed in succession, a single calibration is sufficient.

4 g of hydrophobic granules are made into a paste in a 250 ml glass beaker with 48 g (61 ml) of methanol and the suspension is diluted with 48 g (48 ml) of water and, with the pH electrode immersed, stirred for five minutes with a magnetic stirrer (rotational speed approx. 1000 $min^-$).

Once the stirrer has stopped, the pH value is read after 1 minute's standing. The result is stated to one decimal place.

Determination of Drying Loss

At variance with the sample weight of 10 g stated in DIN ISO 787 II, drying loss is determined using a sample weight of 1 g.

The lid is put on before cooling. Drying is not performed a second time.

While avoiding dusting, approx. 1 g of the sample is weighed out to an accuracy of 0.1 mg into a weighing dish with a ground joint lid which has been dried at 105° C. and the sample is dried for two hours in the drying cabinet at 105° C. After cooling with the lid on over blue gel in a desiccator, weighing is performed again.

$$\%\text{Drying loss at } 105°C. = \frac{G \text{ weight loss}}{g \text{ sample weight}} \times 100$$

The result is stated to one decimal place.

Determination of Ignition Loss (2 h at 1000° C., Relative to Dried Material (2 h at 105° C.)

Basis for Ignition Loss Determination

Ignition loss is determined at 1000° C. At this temperature, the chemically bound water is driven off as well as the physically bound water.

Equipment for Determining Ignition Loss

Porcelain crucible with crucible lid

Muffle furnace

Analytical balances (readability 0.1 mg)

Desiccator

Performance of Ignition Loss Determination

At variance with DIN 55 921, 0.3–1 g of the unpredried material are weighed out to an accuracy of 0.1 mg into a previously calcined porcelain crucible with crucible lid and calcined for 2 hours at 1000° C. in a muffle furnace.

Care must be taken to avoid dusting. It has proved advantageous to place the weighed samples in the muffle furnace while it is still cold.

Slow heating of the furnace avoids relatively severe air turbulence in the porcelain crucibles. Once a temperature of 1000° C. is reached, calcination is continued for a further 2 hours. The sample is then covered with a crucible lid and the crucible placed in a desiccator over blue gel to determine the weight loss.

Evaluation of Ignition Loss Determination

Since ignition loss is determined relative to the sample dried for 2 h at 105° C., the following calculation formula is obtained:

$$\text{Ignition loss} = \frac{m_0 \times \frac{100 - DL}{100} - m_1}{m_0 \times \frac{100 - DL}{100} - m_1} \times 100$$

$m_0$ = sample weight($g$)

$DL$ = drying loss(%)

$m_1$ = weight of calcined sample($g$)

The result is stated to one decimal place.

Production of the Granules According to the Invention

The pyrogenically produced aluminium oxide is dispersed in deionized water using a dispersion apparatus operating on the rotor/stator principle. The resultant dispersions are spray dried. The finished product is separated by means of a filter or cyclone.

The sprayed granules may be heat treated in muffle furnaces. The spray dried and optionally heat treated granules are placed in a mixer for silanization and, while being vigorously mixed, sprayed optionally initially with water and then with the silanising agent. Once spraying is complete, mixing is continued for a further 15 to 30 minutes and heat treatment then performed at 100 to 400° C. for 1 to 4 hours.

The water used may be acidified to a pH value of 7 to 1 with an acid, for example hydrochloric acid. The silanising agent used may be dissolved in a solvent, such ethanol for example.

TABLE 1

Data relating to the spray drying of aqueous $Al_2O_3$ dispersions

| Test number | Quantity $H_2O$ [kg] | Quantity $Al_2O_3$ [kg] | Atomization with | Rotational speed of atomiser disk [rpm] | Operating temperature [° C.] | Exhaust air temperature [° C.] | Spray dryer |
|---|---|---|---|---|---|---|---|
| 1 | 100 | 15 | Single-fluid nozzle | — | 420 | 105 | Niro SD 12.5 |
| 2 | 100 | 10 | Single-fluid nozzle | — | 412 | 102 | Niro SD 12.5 |
| 3 | 5 | 0.75 | Disk | 15 000 | 298 | 1058 | Niro Minor |
| 4 | 16.5 | 2.50 | Disk | 25 000 | 300 | 107 | Niro Minor |
| 5 | 20 | 3.0 | Disk | 35 000 | 300 | 105 | Niro Minor |
| 6 | 8 | 1.2 | Disk | 20 000 | 298 | 106 | Niro Minor |
| 7 | 600 | 90 | Disk | 10 000 | 437 | 100 | Niro SD 12.5 |
| 8 | 300 | 45 | Disk | 20 000 | 458 | 100 | Niro SD 12.5 |
| 9 | 50 | 7.5 | Two-fluid nozzle | — | 260 | 105 | Anhydro Compact |
| 10 | 300 | 45 | Two-fluid nozzle | — | 458 | 108 | Niro SD 12.5 |
| 11 | 200 | 30 | Two-fluid nozzle | — | 457 | 100 | Niro SD 12.5 |
| 12 | 4.25 | 0.75 | Two-fluid nozzle | — | 380 | 105 | Niro Minor |
| 13 | 50 | 5.0 | Two-fluid nozzle | — | 250 | 105 | Anhydro Compact |

TABLE 2

Physicochemical data of the spray dried products

| Test number | Tamped density [g/l] | Drying loss [%] | Ignition loss [%] | pH value | $d_{50}$ value (Cilas) [μm] | Spec. surface area (BET) [m²/g] |
|---|---|---|---|---|---|---|
| 1 | 505 | 2.3 | 2.3 | 5.0 | 39.4 | 99 |
| 2 | 502 | 1.8 | 2.0 | 4.9 | 40.9 | 103 |
| 3 | 473 | 1.4 | 2.7 | 4.9 | 31.1 | 100 |
| 4 | 471 | 1.5 | 2.4 | 5.1 | 20.5 | 95 |

TABLE 2-continued

Physicochemical data of the spray dried products

| Test number | Tamped density [g/l] | Drying loss [%] | Ignition loss [%] | pH value | $d_{50}$ value (Cilas) [μm] | Spec. surface area (BET) [m²/g] |
|---|---|---|---|---|---|---|
| 5 | 466 | 1.5 | 2.6 | 5.0 | 14.5 | 99 |
| 6 | 477 | 1.5 | 1.5 | 5.4 | 27.7 | 98 |
| 7 | 525 | 1.6 | 1.9 | 5.0 | 39.3 | 105 |
| 8 | 474 | 1.5 | 2.8 | 4.8 | 27.6 | 98 |
| 9 | 506 | 3.4 | 2.1 | 5.0 | 28.0 | 99 |
| 10 | 533 | 1.9 | 2.5 | 5.0 | 30.6 | 95 |
| 11 | 516 | 1.8 | 2.5 | 4.7 | 25.8 | 100 |
| 12 | 483 | 1.7 | 2.6 | 4.9 | 8.8 | 101 |
| 13 | 366 | 3.3 | 2.6 | 4.9 | 5.2 | 105 |

TABLE 3

Surface modification of the spray dried products*

| Test number | Surface modifying agent (SMA)** | Parts SMA/100 parts oxide | Parts H₂O/100 parts oxide | Heat treatment temperature [° C.] | Heat treatment time [hours] |
|---|---|---|---|---|---|
| 1 | A | 12 | 5 | 1. 30<br>2. 120 | 1. 6<br>2. 3 |
| 2 | B | 10 | 2.5 | 120 | 2 |
| 3 | C | 10 | 2 | 120 | 3 |
| 4 | D | 10 | 0 | 350 | 2 |
| 5 | E | 15 | 2 | 130 | 2 |
| 6 | F | 10 | 0 | 130 | 2 |
| 7 | B | 15 | 2.5 | 120 | 2 |

**
A = hexamethyldisilazane
B = octyltrimethoxysilane
C = aminopropyltriethoxysilane
D = dimethylpolysiloxane
E = hexadecyltrimethoxysilane
F = 3-methacryloxypropyltrimethoxysilane
*Example 7 from Table 1 was used

TABLE 4

Physicochemical data of the surface modified products

| Test number | Tamped density [g/l] | pH value | Drying loss [%] | Ignition loss [%] | C content [%] |
|---|---|---|---|---|---|
| 1 | 524 | 7.0 | 1.2 | 2.9 | 1.2 |
| 2 | 573 | 3.7 | 1.3 | 6.4 | 3.7 |
| 3 | 585 | 8.5 | 1.1 | 5.6 | 4.2 |
| 4 | 560 | 3.9 | 0.2 | 1.8 | 1.1 |
| 5 | 580 | 4.2 | 0.9 | 8.3 | 5.2 |
| 6 | 593 | 4.6 | 0.5 | 7.1 | 3.2 |
| 7 | 588 | 3.2 | 0.4 | 8.5 | 5.5 |

Obviously, numerous modifications and variations of the present invention are possible in light of the above teachings. It is therefore to be understood that within the scope of the appended claims, the invention may be practiced otherwise than as specifically described herein.

The present invention is based on German patent application serial No. 101 38 574.9, filed on Aug. 6, 2001, and incorporated herein by reference.

What is claimed is:

1. Granules comprising pyrogenically produced aluminium oxide having the following physicochemical characteristics:

| Average grain diameter: | 5.0 to 150 μm |
|---|---|
| Tamped density: | 300 to 1200 g/l. |

2. The granules of claim 1, wherein the average grain diameter is 5.0 to 45 μm.

3. The granules of claim 1, wherein the tamped density is 300 to 500 g/l.

4. The granules of claim 1, wherein the average grain diameter is 5.0 to 45 μm, and the tamped density is 300 to 500 g/l.

5. A process for the production of the granules according to claim 1, comprising dispersing pyrogenically produced aluminium oxide is dispersed in water and then spray drying.

6. The process of claim 5, wherein the granules are further heat treated at a temperature of 150 to 1100° C. for a period of 1 to 8 hours.

7. Granules comprising pyrogenically produced aluminium oxide having the following physicochemical characteristics:

| Average grain diameter: | 5 to 160 μm |
|---|---|
| Tamped density: | 300 to 1200 g/l |
| Carbon content: | 0.3 to 12.0 wt. %. |

8. The granules of claim 7, wherein the tamped density is 300 to 600 g/l.

9. The granules of claim 7, wherein the tamped density is 300 to 600 g/l, and the carbon content is 1.0 to 6.0 wt. %.

10. A process for the production of the granules according to claim 7, comprising dispersing pyrogenically produced aluminium oxide in water, and then spray drying.

11. The process of claim 10, further comprising heating the granules at a temperature of 150 to 1100° C. for a period of 1 to 8 hours and then silanizing the granules.

12. The process of claim 11, wherein the granules are silanized with a halosilane, alkoxysilane, silazanes and/or a siloxane.

13. A method of producing a glass or a ceramic, comprising incorporating the granules of claim 1 into a glass or a ceramic.

14. A method of producing a glass or a ceramic, comprising incorporating the granules of claim 7 into a glass or a ceramic.

15. A method of producing a cosmetic, toner powder, paint or lacquer, comprising incorporating the granules of claim 1 into a cosmetic, toner powder, paint or lacquer.

16. A method of producing a cosmetic, toner powder, paint or lacquer, comprising incorporating the granules of claim 7 into a cosmetic, toner powder, paint or lacquer.

17. A composition selected from the group consisting of a catalyst support, glass, ceramic, abrasive agent, polishing agent, cosmetic, toner powder, paint and lacquer, which comprises the granules of claim 1.

18. A composition selected from the group consisting of a catalyst support, glass, ceramic, abrasive agent, polishing agent, cosmetic, toner powder, paint and lacquer, which comprises the granules of claim 7.

19. An abrasive agent comprising the granules of a claim 1.

* * * * *